(12) United States Patent
Abramovich et al.

(10) Patent No.: US 8,045,181 B2
(45) Date of Patent: Oct. 25, 2011

(54) INSPECTION SYSTEM AND METHOD WITH MULTI-IMAGE PHASE SHIFT ANALYSIS (75) Inventors: Gil Abramovich, Niskayuna, NY (US); Kevin George Harding, Niskayuna, NY (US); Ralph Gerald Isaacs, Cincinnati, OH (US); Guiju Song, Shanghai (CN); Joseph Benjamin Ross, Cincinnati, NY (US); Jianming Zheng, Shanghai (CN)

(73) Assignee: General Electric Company, Niskayuna, NY (US)

( * ) Notice: Subject to any disclaimer, the term of this patent is extended or adjusted under 35 U.S.C. 154(b) by 44 days.

(21) Appl. No.: 12/469,893

(22) Filed: May 21, 2009

(65) Prior Publication Data
US 2010/0296104 A1 Nov. 25, 2010

(51) Int. Cl.
G01B 11/24 (2006.01)
(52) U.S. Cl. ....................................................... 356/601
(58) Field of Classification Search ................. 356/601, 356/603, 604, 613, 610, 237.1–237.6; 250/559.22, 250/559.17, 559.13, 559.16, 559.19
See application file for complete search history.

(56) References Cited

U.S. PATENT DOCUMENTS

| | | | |
|---|---|---|---|
| 4,657,394 A | 4/1987 | Halioua | |
| 4,984,893 A | 1/1991 | Lange | |
| 5,069,549 A | 12/1991 | Harding | |
| 5,189,493 A | 2/1993 | Harding | |
| 5,471,308 A | 11/1995 | Zeien | |
| 5,570,186 A * | 10/1996 | Satzger et al. | 356/613 |
| 5,825,495 A | 10/1998 | Huber | |
| 5,835,218 A | 11/1998 | Harding | |
| 6,040,910 A | 3/2000 | Wu et al. | |
| 6,084,712 A | 7/2000 | Harding | |
| 6,252,623 B1 | 6/2001 | Lu et al. | |
| 6,690,474 B1 * | 2/2004 | Shirley | 356/603 |
| 7,379,193 B2 | 5/2008 | Liu | |

(Continued)

FOREIGN PATENT DOCUMENTS

CN 101469975 7/2009

(Continued)

OTHER PUBLICATIONS

G. Abramovich et al., "Image Enhancement for Phase Shift Analysis Sensors," Two and Three Dimensional Methods for Inspection and Metrology IV, Edited by Peisen S. Huang—Processing of SPIE, vol. 6382, pp. 63820Q1-63820Q10, Oct. 13, 2006.
EP09178145 Search Report, Apr. 15, 2010.
CN101469975 Abstract, Jul. 1, 2009.

*Primary Examiner* — Gregory J Toatley
*Assistant Examiner* — Iyabo S Alli
(74) *Attorney, Agent, or Firm* — Penny A. Clarke (57) ABSTRACT

An inspection system is provided. The inspection system comprises a light source, a grating, a phase shifting unit, an imager, and a processor. The light source is configured to generate light. The grating is in a path of the generated light and is configured to produce a grating image after the light passes through the grating. The phase shifting unit is configured to form and reflect a plurality of phase shifted patterns of the grating image onto an object surface to form a plurality of projected phase shifting patterns. The imager is configured to obtain image data of the projected phase shifted patterns. The processor is configured to reconstruct the object surface from the image data. An inspection method and a phase shifting projector are also presented.

20 Claims, 4 Drawing Sheets

U.S. PATENT DOCUMENTS

| | | |
|---|---|---|
| 7,417,747 B2 | 8/2008 | Liu |
| 7,466,426 B2 | 12/2008 | Tang et al. |
| 7,489,408 B2 * | 2/2009 | Harding et al. .............. 356/603 |
| 7,499,830 B2 | 3/2009 | Harding et al. |
| 2001/0033386 A1 | 10/2001 | Kranz et al. |
| 2007/0109558 A1 | 5/2007 | Harding et al. |

FOREIGN PATENT DOCUMENTS

| | | |
|---|---|---|
| DE | 19545367 | 12/1997 |
| WO | 9627115 | 9/1996 |

* cited by examiner

INSPECTION SYSTEM AND METHOD WITH MULTI-IMAGE PHASE SHIFT ANALYSIS

BACKGROUND OF THE DISCLOSURE

The invention relates generally to inspection systems and methods for inspecting an object. More particularly, the invention relates to inspection systems and methods for inspecting an edge break of an object.

Inspection of features of an object is desirable to ensure that such features are appropriately configured or shaped to achieve suitable mechanical properties. For example, in objects such as turbine airfoils, compressor fans, blade roots etc., a sharp edge break or a discontinuity may result in a section of the object that may wear out quickly or crack when subjected to thermal and/or mechanical stress. Therefore, it is desirable to accurately measure and characterize such edge breaks.

Different existing systems have been used to inspect edge breaks. For example, an edge break is measured using a wax or soft-metal impression of the edge. The impression is then measured using a stylus or a tracer-type of a mechanical gauge. However, such impression process is an offline process, which is generally time consuming and inexact due to challenges in making an accurate replica of the edge break.

Therefore, there is a need for a new and improved inspection system and method for inspecting edge breaks.

BRIEF DESCRIPTION OF THE DISCLOSURE

An inspection system is provided in accordance with one embodiment of the invention. The inspection system comprises a light source, a grating, a phase shifting unit, an imager, and a processor. The light source is configured to generate light. The grating is in a path of the generated light and is configured to produce a grating image after the light passes through the grating. The phase shifting unit is configured to form and reflect a plurality of phase shifting patterns of the grating image onto an object surface to form a plurality of projected phase shifted patterns. The imager is configured to obtain image data of the projected phase shifted patterns. A processor is configured to reconstruct the object surface from the image data.

A phase shifting projector is provided in accordance with another embodiment of the invention. The phase shifting projector comprises a light source, a grating, and a phase shifting unit. The light source is configured to generate light. The grating is in a path of the generated light and is configured to produce a grating image after the light passes through the grating. The phase shifting unit is configured to form and reflect a plurality of phase shifted patterns of the grating image onto an object surface to form a plurality of projected phase shifted patterns.

Another embodiment of the invention is directed to an inspection method. The inspection method comprises projecting light from a light source through a grating to produce a grating image, guiding the grating image through a phase shifting unit to form and reflect a plurality of phase shifted patterns of the grating image onto an area having a linear dimension of less than about ten millimeters, of an object surface to form a plurality of projected phase shifted patterns at an angle relative to the surface normal, obtaining a plurality of image data of the projected phase shifted patterns from the object surface, as viewed from an angle differing from the angle of projection of the phase shifted patterns onto the object surface, and reconstructing the object surface from the image data with a resolution of less than about ten microns.

These and other advantages and features will be more understood from the following detailed description of preferred embodiments of the invention that is provided in connection with the accompanying drawings.

DETAILED DESCRIPTION OF THE INVENTION

Preferred embodiments of the present disclosure will be described hereinbelow with reference to the accompanying drawings. In the following description, well-known functions or constructions are not described in detail to avoid obscuring the disclosure in unnecessary detail.

Figure 1:
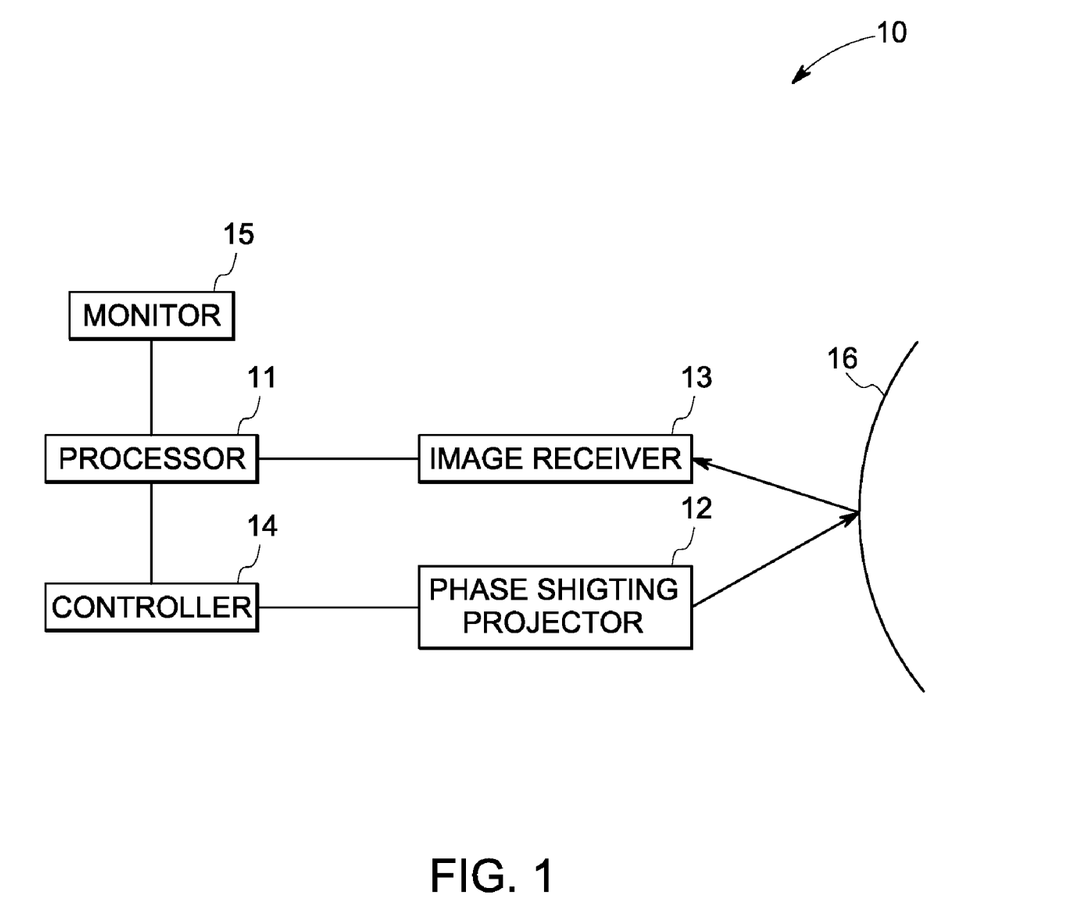
FIG. 1 is a schematic diagram of an inspection system for inspecting an object surface in accordance with one embodiment of the invention.

FIG. 1 depicts a schematic diagram of an inspection system 10 for inspecting features of an object surface 16 in accordance with one embodiment of the invention. As used herein, the term "features" may comprise corrosion, pitting, edges, surface textures, and other geometric features. In the illustrated embodiment, the inspection system 10 comprises a processor 11, a phase shifting projector 12, an image receiver 13, a controller 14, and a monitor 15. Although the object surface 16 is shown as being spherical, the invention is not limited to any specific type of object surface, and the object surface can be any shape. In some embodiments, the phase shifting projector 12 and the image receiver 13 may point at the same region of interest on the object surface 16 with a relative angle therebetween.

For the illustrated arrangement, the processor 11 may comprise a central processing unit (CPU) for processing images captured by the image receiver 13 from the object surface 16. The controller 14 is connected to the processor 11 and may comprise an electrical and/or mechanical system, such as a solenoid, a step motor, or a programmed actuator including a piezoelectric actuator, to control the phase shifting projector 12 to produce the desired phase shifted patterns. In other examples, the controller 14 may not be directly coupled to the processor 11, and instead may control the phase shifting project 12 independently. The monitor 15 may comprise a display, such as, for example, a liquid crystal display (LCD), to display a final measured image of the object surface 16 for users to observe.

It should be noted that the present invention is not limited to any particular processor for performing the processing tasks of the invention. The term "processor", as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output, as will be understood by those skilled in the art.

Figure 2:
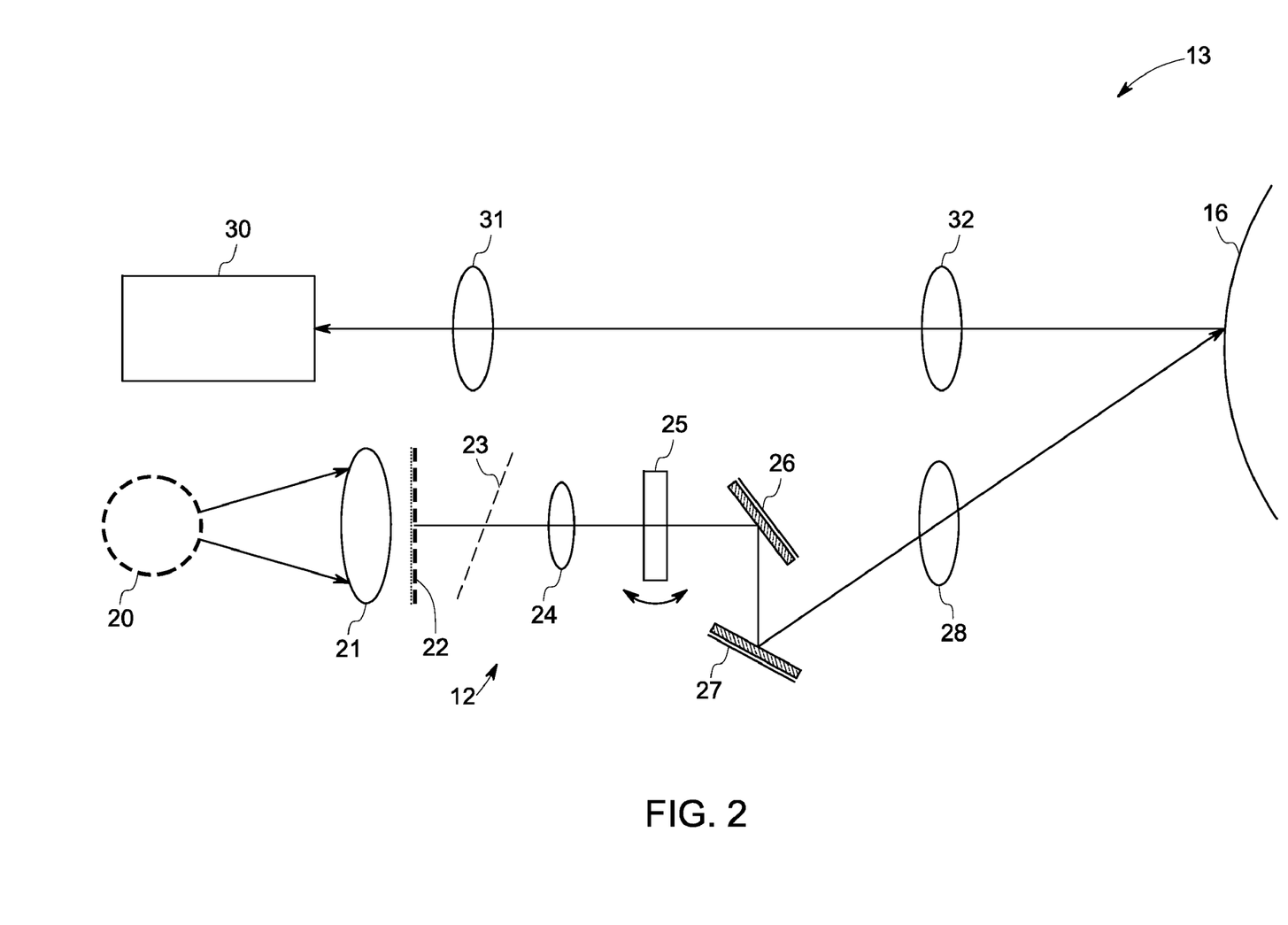
FIG. 2 is a schematic diagram of a phase shifting projector and an image receiver shown in FIG. 1, in accordance with one embodiment of the invention.

FIG. 2 shows a schematic diagram of the phase shifting projector 12 and the image receiver 13 shown in FIG. 1 according to one embodiment of the invention. As illustrated in FIG. 2, the phase shifting projector 12 includes a light source 20, condensing optics 21, a diffuser 22, a grating 23, first relay optics 24, a first phase shifting unit (not labeled), and projecting optics 28. The first phase shifting unit includes a rotatable transparent plate 25, a first mirror 26, and a second mirror 27. As used herein, the term "mirror" denotes any suitable elements that can reflect desired phase shifted patterns onto the object surface 16. Additionally, the image receiver 13 includes an imager 30, second relay optics 31, and viewing optics 32.

In the illustrated example, the light source 20 typically comprises a white light source, but may include any appropriate light source, such as a mercury or metal halide arc lamp, a halogen lamp, a laser/phosphor system, a fiber coupled laser, or a LED based light source. The first and second relay optics 24, 31, the projecting optics 28, and the viewing optics 32 may comprise conventional lenses, or any lens with high efficiency, low distortion, and good focus. The transparent plate 25 may comprise a glass plate. The imager 30 may comprise a charge-coupled device (CCD) sensor or any other device having a two-dimensional array of light-sensitive pixels that outputs a video signal in response to the light level sensed at each pixel.

In one non-limiting example, the first and second relay optics 24, 31 may comprise a variable focus relay lens respectively. The first and second mirrors 26, 27 may be stationary. The projecting optics 28 may comprise a microlens. In some examples, the projecting optics 28 may comprise a microlens configured to image the grating pattern(s) onto a small area of the object surface with high spatial resolution in a manner similar to a microscope system. The viewing optics 32 may comprise an objective lens. In one example, the viewing optics 32 comprises a telecentric lens. In certain examples, the viewing optics 32 are configured to view a small area of the object surface with high spatial resolution in a manner similar to a microscope system. In more particular embodiments, the viewing optics 32 are configured to view an area having a linear dimension of a few millimeters in size of the object surface, for example, of less than about ten millimeters in size, with a high spatial resolution of less than about ten microns.

As depicted in FIG. 2, during operation, the light source 20 generates light beams (not labeled). The condensing lens 21 converges the light beams to produce converging beams. The converging beams pass through the diffuser 22 to produce uniform beams. The uniform beams pass through the grating 23 to produce fringe beams. The variable focus lens 24 transmits the fringe beams to pass through the rotatable transparent plate 25 to reach the first mirror 26. The first mirror 26 then reflects the fringe beams to the second mirror 27, and the second mirror 27 continues to reflect the fringe beams to pass through the projecting lens 28, so that a grating image or fringe pattern of the grating 23 is projected onto the object surface 16. In one non-limiting example, the phase shifting unit 12 is further configured to form the projected phase shifted patterns at an angle relative to a surface normal to the object surface 16, and the imager 30 is further configured to obtain image data of the projected phase shifted patterns as viewed from an angle differing from the angle of projection of the phase shifting unit 12.

After the fringe pattern is projected onto the object surface 16, the geometry of the object surface 16 may distort the fringe pattern of the grating 22. The objective lens 32 guides and focuses a reflection of the projected fringe pattern from the object surface 16 to the variable focus relay lens 31. The variable focus relay lens 31 transmits the projected fringe pattern into the imager 30 to get image data in the projected fringe pattern. Finally, the image data is processed in the processor 11 (shown in FIG. 1) to prepare for reconstructing the contour of the object surface 16.

As depicted in FIG. 1, the controller 14 may control the rotatable transparent plate 25 to rotate by a certain angle each time. In one non-limiting example, the controller 14 comprises a piezoelectric actuator for controlling the rotatable transparent plate 25 to rotate about an axis (not shown) parallel to grid lines of the grating 23. Accordingly, in some embodiments, with the movement of the rotatable transparent plate 25, a plurality of different phase shifted fringe patterns of the grating image can be generated one by one over a short period of time. In the meantime, the imager 30 also retrieves the projected phase shifted fringe patterns one by one. The processor 11 processes the different projected phase shifted fringe patterns to reconstruct the object surface 16.

For the illustrated arrangement in FIG. 2, the first and second mirrors 26, 27 fold the fringe pattern(s) of the grating 23, and cooperate with the first relay lens 24 and the projecting lens 28 so that the inspection system 10 may map the contour of small features on the object surface 16 in high resolution. Additionally, the image receiver 13 employs the second relay lens 31 and the objective lens 32 to reach a high-resolution light collection of the small features on the object surface 16.

Figure 3:
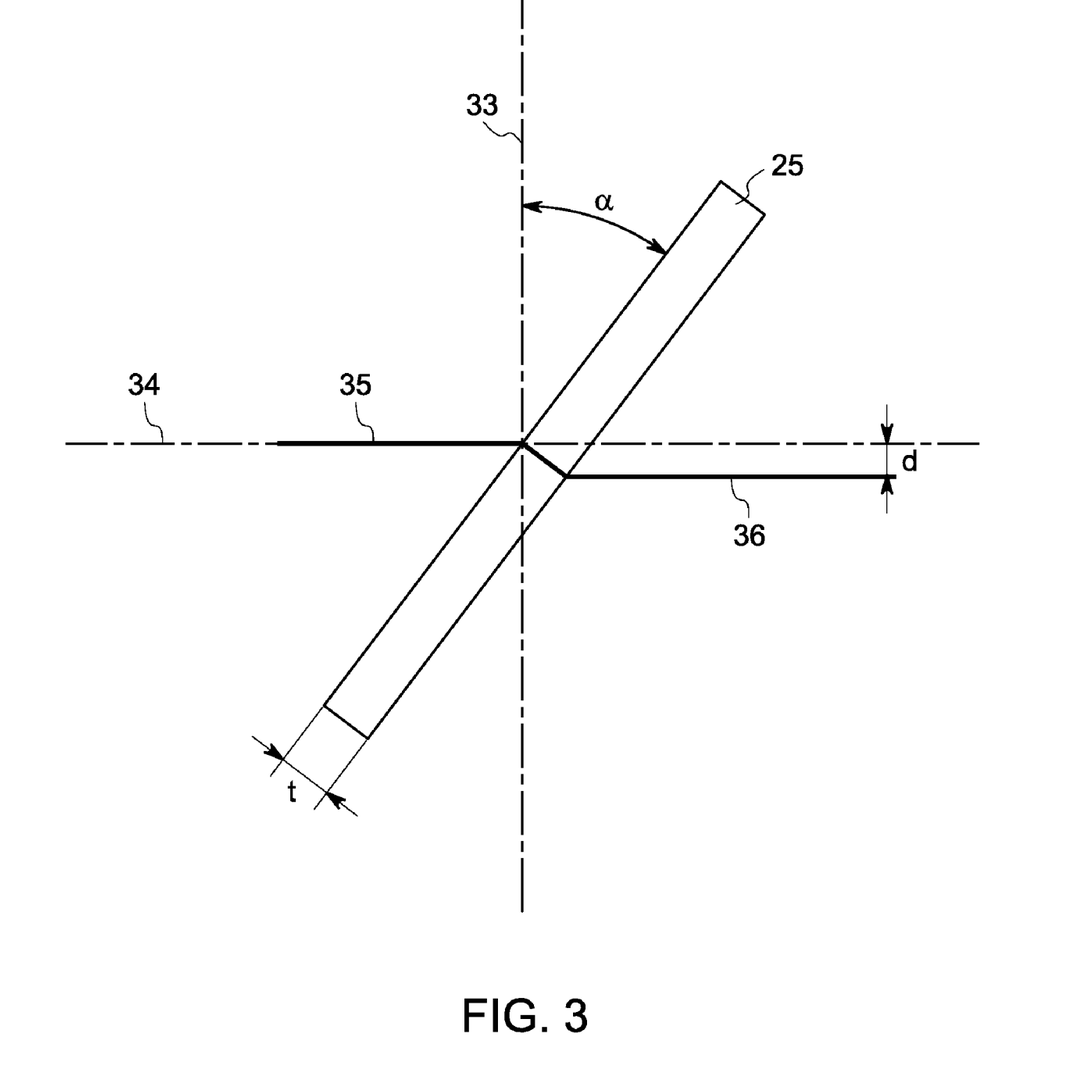
FIG. 3 is a schematic diagram showing the operation of rotating a rotatable plate to accomplish phase shifting.

FIG. 3 illustrates a schematic diagram showing the operation of rotating the rotatable transparent plate 25 to accomplish phase shifting. As illustrated in FIG. 3, the rotatable transparent plate 25 is tilted by an angle α relative to a plane 33 perpendicular to an axis 34, so an incident beam 35 parallel to the axis 34 is refracted inside the rotatable transparent plate 25 and a transmitted beam 36 is parallel to and displaced a distance "d" relative to the incident beam 35. It is known to one skilled in the art that when the displacement "d" is 1/N (N is integer and N≧3) of a grating period of a given grating, a phase shift angle of one pattern is 2π/N relative to an adjacent pattern. In one embodiment, the thickness of the rotatable transparent plate 25 is "t," and its index of refraction is "n." The displacement "d" of the incident beam 35 is given by the following equation:

$$d = t \cdot \sin a \left[ 1 - \frac{\cos a}{(n^2 - \sin^2 a)^{\frac{1}{2}}} \right].$$

Therefore, by controlling the angle α, one may readily determine the phase shift angle of one fringe pattern relative to an adjacent fringe pattern.

It is desirable to avoid adding too much optical aberration to the phase shifting projector 12. A tilted rotatable plate in a diverging optical beam produces various amounts of spherical and astigmatism aberrations to the projecting image. The thicker the glass plate and the larger the tilted angle α, the greater the magnitude of the added aberrations. The product designer may check the optical design of the image of the phase shifting projector to determine if the added aberrations are tolerable in their effects on the projected image.

Additionally, accuracy of the inspection system 10 may be largely determined by its baseline spacing. In one embodiment, the baseline spacing is the spacing between the projecting lens 28 and the viewing lens 32. The greater the distance between the projecting lens 28 and the viewing lens 32, the higher the measurement resolution of the inspection system 10. Therefore, in order to increase the system's resolution, when both the projecting lens 28 and the viewing lens 32 are disposed in an end (not shown) of the inspection system 10, the projecting lens 28 is disposed on one side while the viewing lens 32 is disposed on the other side of the end of the inspection system 10.

In some embodiments, the fringe patterns of the grating 23 may include parallel light and dark lines comprising sinusoidal intensity profiles. Patterns having square, trapezoidal, triangular, or other profiles may be projected onto the object surface 16. In other embodiments, the patterns need not comprise straight, parallel lines. For example, curved lines, wavy lines, zigzagging lines, or other such patterns may be used with appropriate phase shift analysis. In one non-limiting example, when the grid lines of the grating 23 have a square-wave distribution, the patterns are square-waves (square profiles) too, which may introduce some non-linearity errors in the phase shift calculation. The projecting lens 28 may work as a spatial band-pass filter to change the square-waves to sinusoidal waves to decrease the non-linearity errors.

In certain embodiments, the reconstruction of the object surface 16 is accomplished by using any of the traditional algorithms known from phase shift analysis to first combine the information from the phase shifted patterns to acquire a phase-wrapped image, and then unwrapping the phase-wrapped image to reconstruct the object surface 16 in the processor 11.

In one embodiment, a three-step phase-shifting algorithm is used to reconstruct the object surface 16. As illustrated in FIGS. 2-3, three phase shifted patterns are generated with each phase shifted pattern being generated at a separate phase shift angle by rotating the rotatable transparent plate 25. In one example, the phase shift patterns are separated by 120° degrees ($2\pi/3$), so, the three separate phase shift angles may be $-2\pi/3$, 0, and $2\pi/3$. Intensity I(x, y) of each point in the three different patterns can be respectively represented as follows:

$$I_1(x,y)=A+M \cos [\phi(x,y)-2\pi/3]$$

$$I_2(x,y)=A+M \cos [\phi(x,y)]$$

$$I_3(x,y)=A+M \cos [\phi(x,y)+2\pi/3]$$

where A is the average intensity, M is the intensity modulation, and $\phi(x, y)$ is the wrapped phase to be determined. Solving the above three equations for $\phi(x, y)$ simultaneously yields the following solution:

$$\phi(x, y) = \arctan\left(\frac{\sqrt{3}(I_1 - I_3)}{2I_2 - I_1 - I_3}\right).$$

With the intensity $I_1$, $I_2$, and $I_3$ known, the wrapped phase $\phi(x, y)$ of the each point is determined, and its range is between $-\pi$ and $\pi$. Then, the wrapped phase $\phi(x, y)$ of each point is unwrapped by known phase unwrapping processes to obtain its absolute phase. Then, the actual height coordinate Z(x, y) of the point can be determined by its absolute phase and system parameters, which are known to those skilled in the art. In this manner, the object surface 16 can be reconstructed, yielding accurate measurements.

Figure 4:
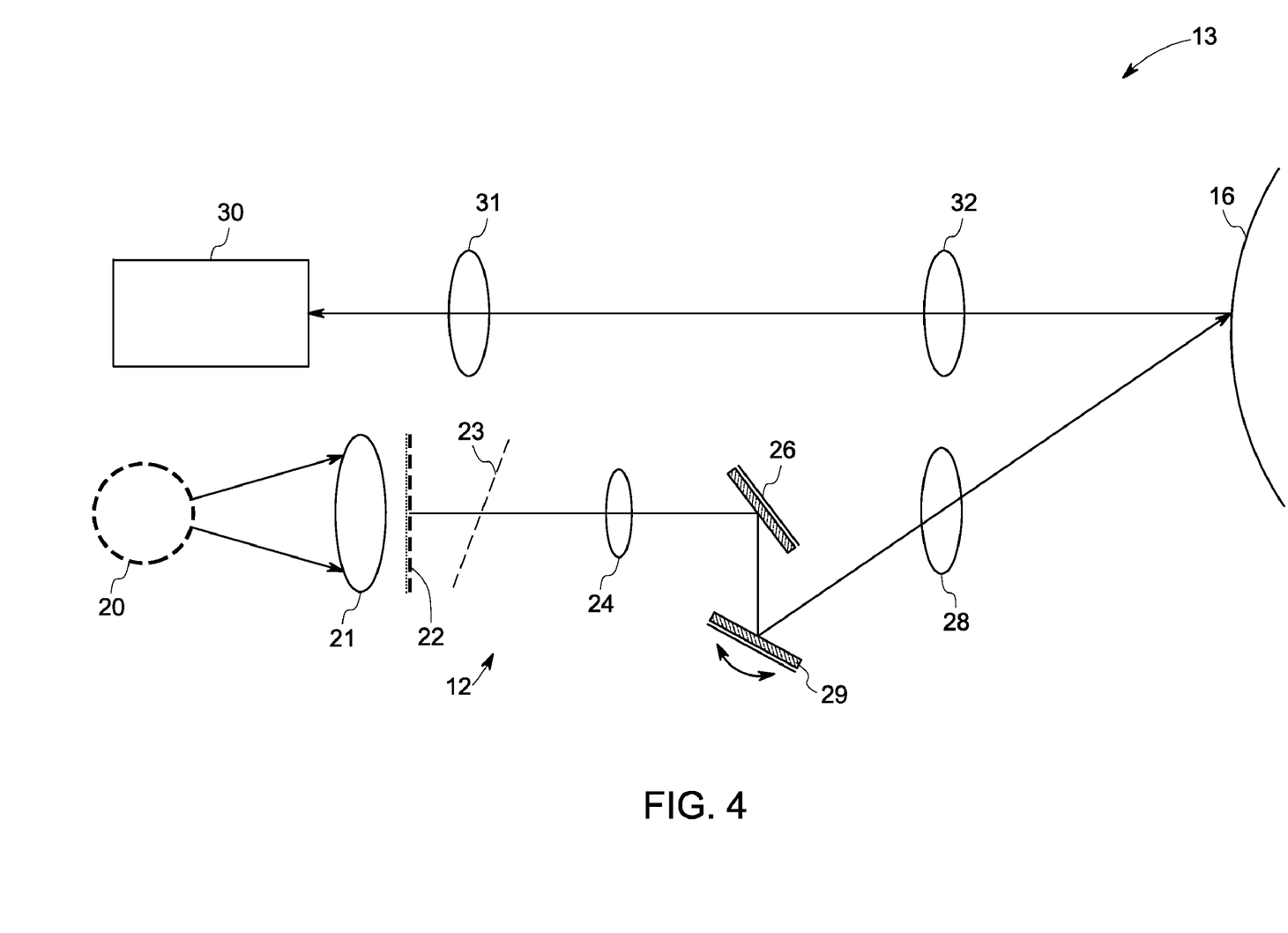
FIG. 4 is a schematic diagram of the phase shifting projector and the image receiver shown in FIG. 1, in accordance with another embodiment of the invention.

FIG. 4 shows a schematic diagram of the phase shifting projector 12 and the image receiver 13 shown in FIG. 1 according to another embodiment of the invention. The configuration of the illustrated embodiment is similar to that shown in FIG. 2, and the same reference numerals in FIGS. 2 and 4 are used to indicate the same elements. The two illustrated embodiments shown in FIGS. 2 and 4 differ in that the second phase shifting unit (not labeled) shown in FIG. 4 does not employ the rotatable transparent plate 25 (shown in FIG. 2) but instead employs the first mirror 26 and a rotatable mirror 29. In certain examples, the first mirror 26 may be stationary.

Accordingly, as depicted in FIG. 4, the first relay lens 24 transmits the fringe beams from the grating 23 to reach the first mirror 26. The first mirror 26 reflects the fringe beams to the rotatable mirror 29, and the rotatable mirror 29 continues to reflect the fringe beams to pass through the projecting lens 28 so that a grating image or fringe pattern of the grating 23 is projected onto the object surface 16. Thus, a plurality of different phase shifted patterns of the grating image of the grating 22 are generated one by one by rotating the rotatable mirror 29 over a short period of time, which can be implemented by one skilled in the art. Similarly, the image receiver 13 may retrieve the projected different phase shifted patterns so that the processor 11 reconstructs the contour of the object surface 16.

In some embodiments, the controller 13 may control movement of the rotatable mirror 29. In one embodiment, the controller 13 comprises a piezoelectric actuator to control the movement of the rotatable mirror 29, which together may be referred to as a tilting piezo mirror. In this manner, the inspection system may inspect the features of the object surface 16 with high resolution.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. An inspection system, comprising:
a light source configured to generate light;
a grating in a path of the generated light and configured to produce a grating image after the light passes through the grating;
a phase shifting unit configured to form and reflect a plurality of phase shifted patterns of the grating image onto an object surface to form a plurality of projected phase shifted patterns;
an imager configured to obtain image data of the projected phase shifted patterns; and
a processor configured to reconstruct the object surface from the image data.

2. The inspection system of claim 1, wherein the phase shifting unit comprises a first phase shifting unit or a second phase shifting unit, wherein the first phase shifting unit comprises a rotatable transparent plate and a pair of mirrors, and wherein the second phase shifting unit comprises a pair of mirrors.

3. The inspection system of claim 2, wherein the rotatable transparent plate of the first phase shifting unit is configured to form and transmit the phase shifted patterns of the grating image to the mirrors of the first phase shifting unit, and wherein the mirrors of the first phase shifting unit are stationary and configured to reflect the phase shifted patterns onto the object surface.

4. The inspection system of claim 2, wherein the mirrors of the second phase shifting unit comprises a stationary mirror and a rotatable mirror, and wherein the stationary mirror is configured to reflect the grating image onto the rotatable mirror, and the rotatable mirror is configured to form the phase shifted patterns of the grating image.

5. The inspection system of claim 1, further comprising a controller configured to control the phase shifting unit to form the phase shifted patterns, and wherein the controller comprises a piezoelectric actuator.

6. The inspection system of claim 1, further comprising:
a plurality of projecting optics configured to project the phase shifted patterns from the phase shifting unit onto the object surface; and
a plurality of viewing optics configured to guide and focus the projected phase shifted patterns from the object surface onto the imager.

7. The inspection system of claim 6, wherein the viewing optics comprise a telecentric lens and the projecting optics comprise a microlens.

8. The inspection system of claim 6, further comprising a first variable focus relay lens located between the grating and the phase shifting unit, and a second variable focus relay lens located between the viewing optics and the imager.

9. The inspection system of claim 1, further comprising a condensing lens located between the light source and the grating, and a diffuser located between the condensing lens and the grating.

10. The inspection system of claim 1, wherein the inspection system inspects an area having a linear dimension of less than about ten millimeters in size on the object surface with a resolution of less than about ten microns.

11. The inspection system of claim 1, wherein the phase shifting unit is further configured to form the projected phase shifted patterns at an angle relative to a surface normal to the object surface, and wherein the imager is further configured to obtain the image data of the projected shifted patterns as viewed from an angle differing from the angle of projection of the phase shifting unit.

12. A phase shifting projector, comprising:
a light source configured to generate light;
a grating in a path of the generated light and configured to produce a grating image after the light passes through the grating; and
a phase shifting unit configured to form and reflect a plurality of phase shifted patterns of the grating image onto an object surface to form a plurality of projected phase shifted patterns.

13. The phase shifting projector of claim 12, wherein the phase shifting unit comprises a first phase shifting unit or a second phase shifting unit, wherein the first phase shifting unit comprises a rotatable transparent plate and a pair of mirrors, and wherein the second phase shifting unit comprises a pair of mirrors.

14. The inspection system of claim 13, wherein the rotatable transparent plate of the first phase shifting unit is configured to form and transmit the phase shifted patterns of the grating image to the mirrors of the first phase shifting unit, wherein the mirrors of the first phase shifting unit are stationary and configured to reflect the phase shifted patterns onto the object surface, wherein the mirrors of the second phase shifting unit comprises a stationary mirror and a rotatable mirror, and wherein the stationary mirror is configured to reflect the grating image onto the rotatable mirror, and the rotatable mirror is configured to form the phase shifted patterns of the grating image.

15. The phase shifting projector of claim 12, further comprising a plurality of projecting optics configured to project the phase shifted patterns from the phase shifting unit onto an area having a linear dimension of less than about ten millimeters, of the object surface and a first variable focus relay lens located between the grating and the phase shifting unit.

16. An inspection method, comprising:
projecting light from a light source through a grating to produce a grating image;
guiding the grating image through a phase shifting unit to form and reflect a plurality of phase shifted patterns of the grating image onto an area having a linear dimension of less than about ten millimeters, of an object surface to form a plurality of projected phase shifted patterns at an angle relative to the surface normal;
obtaining a plurality of image data of the projected phase shifted patterns from the object surface, as viewed from an angle differing from the angle of projection of the phase shifted patterns onto the object surface; and
reconstructing the object surface from the image data with a resolution of less than about ten microns.

17. The inspection method of claim 16, wherein the phase shifting unit comprises a first phase shifting unit or a second phase shifting unit, wherein the first phase shifting unit comprises a rotatable transparent plate and a pair of mirrors, and wherein the second phase shifting unit comprises a pair of mirrors.

18. The inspection method of claim 17, wherein the rotatable transparent plate of the first phase shifting unit is configured to form and pass the phase shifted patterns of the grating image to the mirrors of the first phase shifting unit, and wherein the mirrors of the first phase shifting unit are stationary and are configured to reflect the phase shifted patterns onto the object surface.

19. The inspection method of claim 17, wherein the mirrors of the second phase shifting unit comprises a stationary mirror and a rotatable mirror, and wherein the stationary mirror is configured to reflect the grating image onto the rotatable mirror, and the rotatable mirror is configured to form the phase shifted patterns of the grating image.

20. The inspection method of claim 16, further comprising guiding the phase shifted patterns through a projection lens for projection onto the object surface after being formed and reflected from the phase shifting unit, guiding the projected phase shifted patterns through a viewing lens before being imaged onto the imager, guiding the light through a condensing lens and a first variable focus relay lens before passing through the grating, and guiding the projected shifted patterns through a second variable focus relay lens after passing through the viewing lens.

* * * * *

UNITED STATES PATENT AND TRADEMARK OFFICE
CERTIFICATE OF CORRECTION

PATENT NO. : 8,045,181 B2  
APPLICATION NO. : 12/469893  
DATED : October 25, 2011  
INVENTOR(S) : Abramovich et al.

Page 1 of 1

It is certified that error appears in the above-identified patent and that said Letters Patent is hereby corrected as shown below:

On the Face Page, in the Figure, for Tag "12", Line 1, delete "SHIGTING" and insert -- SHIFTING --, therefor.

In Fig. 1, Sheet 1 of 4, for Tag "12", Line 1, delete "SHIGTING" and insert -- SHIFTING --, therefor.

In Column 7, Line 51, in Claim 14, delete "inspection system" and insert -- phase shifting projector --, therefor.

Signed and Sealed this  
Twenty-first Day of February, 2012

David J. Kappos  
*Director of the United States Patent and Trademark Office*